US00PP30426P2

(12) United States Plant Patent
Bagdasarian

(10) Patent No.: US PP30,426 P2
(45) Date of Patent: Apr. 23, 2019

(54) STRAWBERRY PLANT NAMED 'SANGRIA'

(50) Latin Name: ***Fragaria* x *ananassa***
Varietal Denomination: Sangria

(71) Applicant: Jimmy Haig Bagdasarian, Santa Cruz, CA (US)

(72) Inventor: Jimmy Haig Bagdasarian, Santa Cruz, CA (US)

(73) Assignee: Lassen Canyon Nursery, Inc., Redding, CA (US)

( * ) Notice: Subject to any disclaimer, the term of this patent is extended or adjusted under 35 U.S.C. 154(b) by 0 days.

(21) Appl. No.: 15/732,842

(22) Filed: Jan. 3, 2018

(51) Int. Cl.
*A01H 5/08* (2018.01)

(52) U.S. Cl.
USPC ..... Plt./208
CPC ..... *A01H 5/08* (2013.01)

(58) Field of Classification Search
USPC ..... Plt./208, 209
CPC ..... A01H 5/0893
See application file for complete search history.

(56) References Cited

U.S. PATENT DOCUMENTS

| | | |
|---|---|---|
| PP22,472 P3 | 1/2012 | Bagdasarian |
| PP26,974 P3 | 7/2016 | Bagdasarian |
| PP27,034 P3 | 8/2016 | Bagdasarian |
| PP27,190 P3 | 9/2016 | Bagdasarian |

*Primary Examiner* — Kent L Bell
(74) *Attorney, Agent, or Firm* — Phase M Legal

(57) ABSTRACT

A new and distinct variety of strawberry plant (*Fragaria* x *ananassa*) named 'Sangria' is presented here. This new short-day strawberry variety is characterized by a medium vigor plant which produces large, attractive, semi-glossy, long conical to occasionally wedge-shaped berries with a sweet strawberry flavor and a desirable lighter red color in the interior and exterior. 'Sangria' is firmer than its parents, allowing for better transport. While still rare, this variety does tend to have a higher than usual propensity to have leaves with four leaflets as compared with other varieties. The variety, while short-day, is partially remontant in cool coastal environments of California.

7 Drawing Sheets

Latin name of the genus and species of the plant claimed: Botanical classification: *Fragaria* x *ananassa*.

Variety denomination: The new strawberry variety denomination is 'Sangria.'.

BACKGROUND OF THE INVENTION

Field of Invention

The present invention relates to a new and distinct strawberry variety named 'Sangria.' This new short-day variety is the result of a controlled cross in an ongoing breeding program by the inventor, Jimmy Bagdasarian, in 2009. The variety is botanically known as *Fragaria* x *ananassa*. The primary market of this variety is for the fresh market sales of the fruit. 'Sangria' produces large, conical to occasionally wedge-shaped berries, which are medium firm, have good flavor and a light red color.

Comparison with Parent Varieties

The controlled cross which produced 'Sangria' was the result of a cross in 2009 between a strawberry variety used as a female parent designated '3F64' (an unreleased proprietary variety), and a strawberry variety used as the male pollen parent designated 'Sweet Ann' (U.S. Plant Pat. No. 22,472).

The characteristics of the female parent '3F64' are: A short-day plant with partial remontant tendencies in coastal regions. It has dark green glossy leaves with little blistering and an open architecture. The plant has high vigor, more than 'Sangria.' The fruit of '3F64' are medium firm, medium sized with a slightly dull appearance. '3F64' fruit are medium red colored with a slightly lighter center in the interior of the fruit. Fruit shape is mostly conical with few creases and with a few wedge-shaped fruits.

The male pollen parent 'Sweet Ann' has the following characteristics: A day neutral plant with an open plant density and a high vigor plant, substantially higher in vigor than that of 'Sangria.' The leaves are medium glossy with little to no blistering. Fruit of 'Sweet Ann' are very large (larger than that of 'Sangria'), conical, and sweet, with a glossy medium red color on the interior and exterior, often with a white shoulder near the calyx.

'Sangria' is a short-day plant, unlike its male parent 'Sweet Ann,' but similar to its female parent '3F64.' Both parents of 'Sangria' have high vigor, while 'Sangria' has medium vigor. The fruit size of 'Sangria' falls between both parents, larger than the fruit of '3F64,' but smaller than that of 'Sweet Ann.' The firmness of 'Sangria' fruit, however, are slightly firmer than that of both parents. Fruit shape of 'Sangria' are more attractive than that of its female parent '3F64,' but similar in attractiveness to 'Sweet Ann' fruit.

The cross done to create 'Sangria' was carried out in Santa Cruz, Calif., USA. Pollen taken from 'Sweet Ann' was placed onto a flower with male parts removed on '3F64' and then covered so that no other pollen could contaminate the procedure. Once the berry began to develop, the covering was removed. Ripe strawberries were then harvested, and the seed was extracted and germinated in a greenhouse in Redding, Calif., USA. The resulting seedlings were transplanted to Shastina, Calif. in 2010, grown out for an additional period, allowing them to propagate asexually through runners. Clones were then harvested and planted in breeding plots in fruiting fields in late September in: Oxnard, Calif. (Ventura County), and mid-October in Watsonville, Calif. (Monterey County). The selection of the new variety was first made in Watsonville, Calif., and given the designation '10K52' in 2011. This selection was later named 'Sangria.'

The variety was further propagated asexually by runners (stolens) in breeding plots in: Macdoel, Calif. (Siskiyou County), and Manteca, Calif. (San Joaquin County). The new variety has also been "meristemed." Small pieces of plant material of approximately 0.5 mm in diameter and consisting of the undifferentiated meristem tissue and one or two leaf primordia were removed from the buds on crowns of young daughter plants, then placed on nutrient medium, and new plants were grown from them. Planting stock from the "meristemed" plants are growing in a screenhouse located in Redding, Calif. These propagules of 'Sangria' are identical to the original plant in all distinguishing characteristics. The propagation has been monitored throughout the process, and all traits disclosed herein remain fixed and true to type through successive generations of asexual reproduction.

SUMMARY OF THE INVENTION

'Sangria' is a short-day variety exhibiting the following combination of characteristics, which have been observed repeatedly, and which distinguish this strawberry plant as a new and distinct variety:

1. The variety produces large sized fruit;
2. The fruit is well shaped, long-conical to occasionally wedge shaped;
3. The fruit is attractive, having a semi-glossy, medium red exterior and interior;
4. The fruit is sweet tasting, with good flavor;
5. The variety produces a high volume of fruit;
6. The plants of the variety maintain a semi-open architecture; and,
7. The variety is partially remontant in a cool, coastal environment.

'Sangria' fruit demonstrates characteristics and qualities that are desired by fresh market strawberry sales companies. The lighter, medium red color is preferred by many shippers of fresh strawberries, as darker berries are more likely to be viewed as overripe by buyers than the lighter colored fruit. 'Sangria' fruit is larger than that of its female parent '3F64,' but smaller than that of its paternal parent 'Sweet Ann.' The ripening pattern of 'Sangria' is an improvement on that of 'Sweet Ann,' as it ripens more fully to the top of the berry, unlike 'Sweet Ann' which often has a shoulder that does not ripen. In addition, 'Sangria' fruit is firmer than its parents 'Sweet Ann' and '3F64,' allowing it to hold up better in transit. While still mostly a long-conical shape, fruit of 'Sangria' is not as long as 'Sweet Ann' making it easier to pack. The plant vigor of 'Sangria' is medium which provides an advantage over higher vigor varieties in that berries are easier to see and therefore pick. This lower vigor also allows for better spray coverage when controlling for pests.

BRIEF DESCRIPTION OF THE DRAWINGS

The accompanying color photographs, identified as FIGS. 1 through 7, show the appearance of typical specimens of the new strawberry variety, initially designated '10K52,' and now named 'Sangria.' These figures depict the colors, as nearly true as it is reasonably possible given differences in color illustrations of this character. Accordingly, color in the photographs may differ slightly from the colors discussed in the botanical description. The photographs of the depicted plant, plant parts, and fruit of 'Sangria' were taken in October/November of 2017.

DETAILED BOTANICAL DESCRIPTION OF THE PLANT

Figure 1:
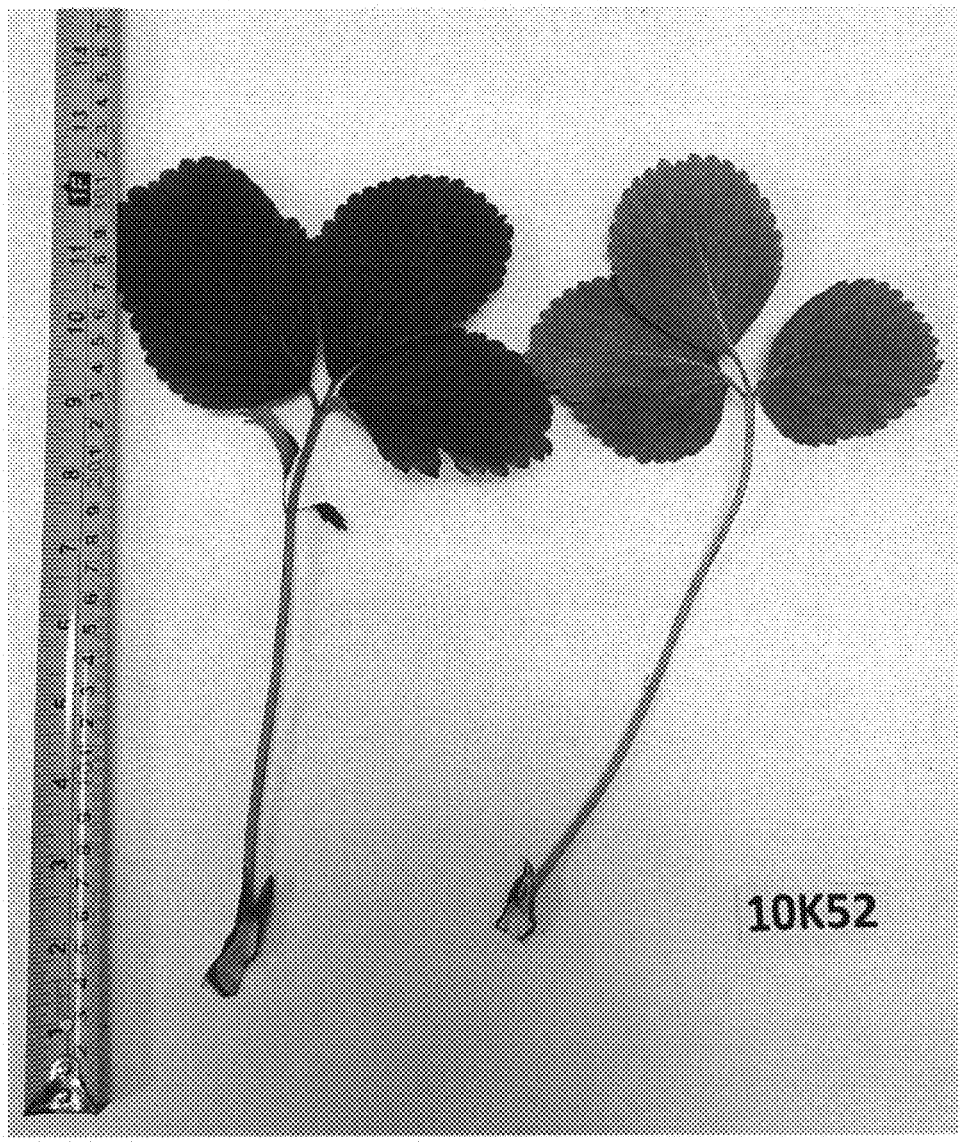
FIG. 1 shows the top and bottom of a typical leaf and petiole structure.
Figure 2:
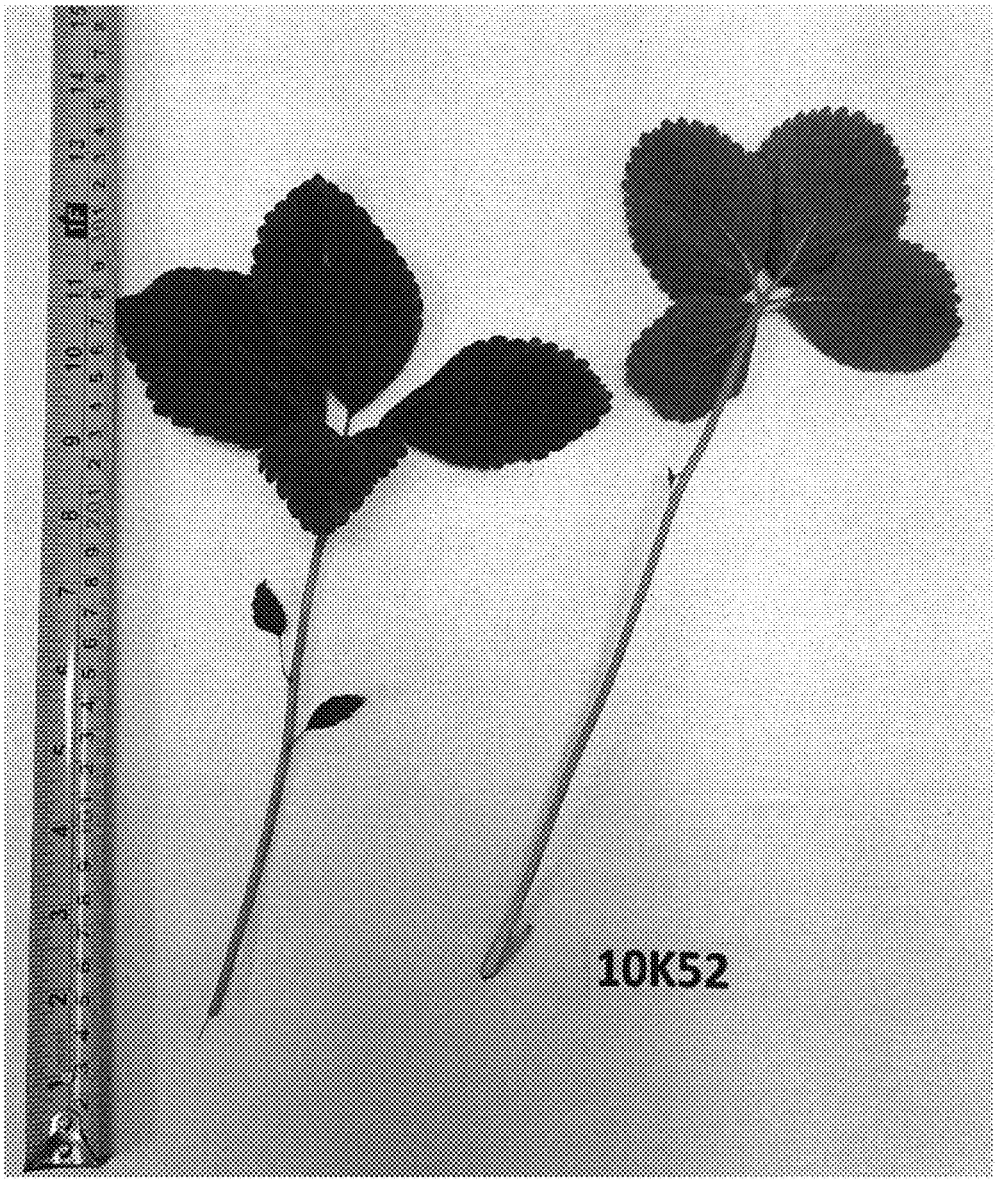
FIG. 2 shows the top and bottom of typical, and rarer, leaf structure with more leaflets.
Figure 3:
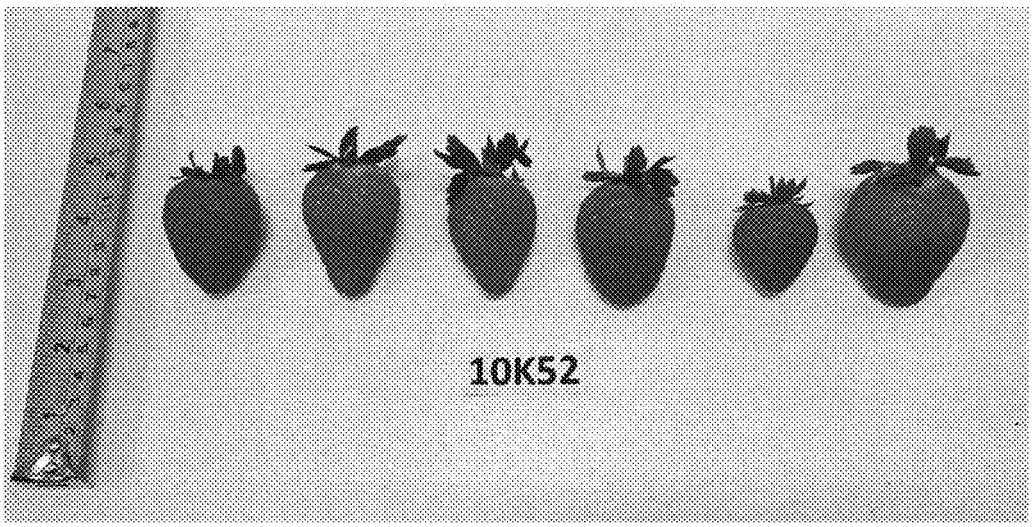
FIG. 3 shows a selection of typical late-season fruit.
Figure 4:
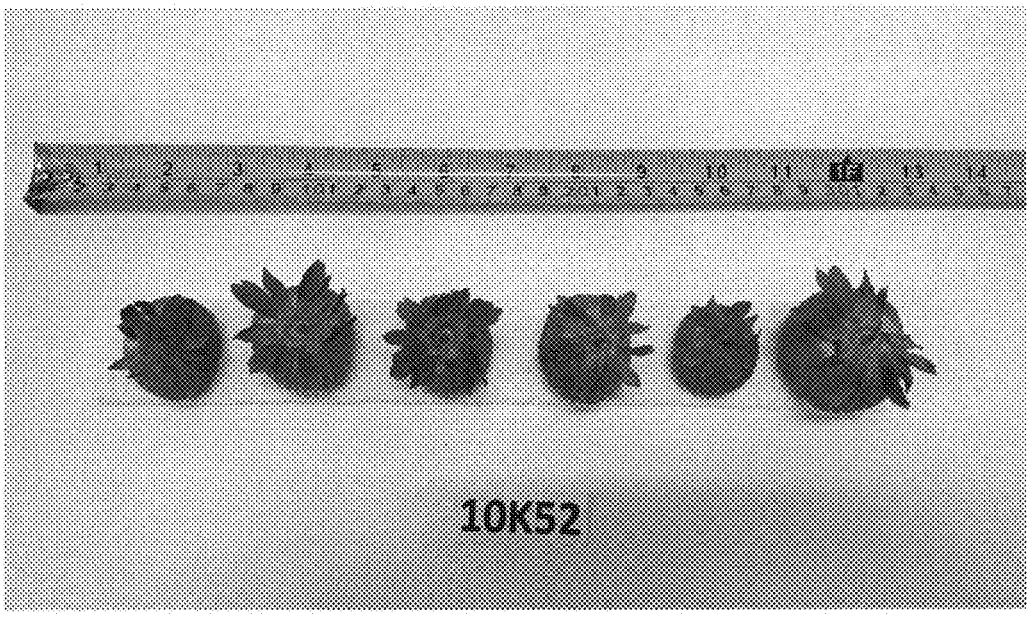
FIG. 4 shows typical fruit shape and calyx position over the berry of 'Sangria'.
Figure 5:
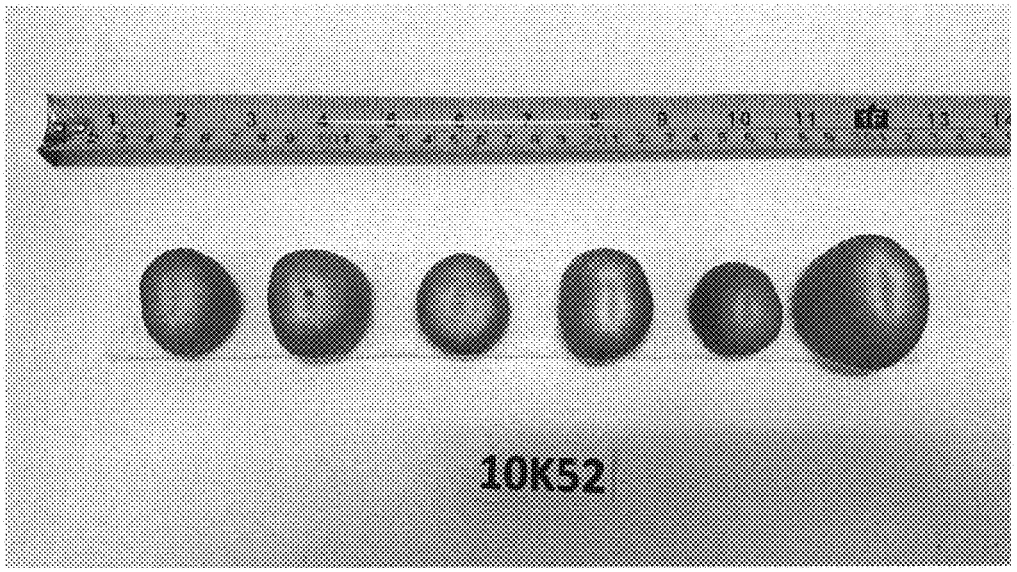
FIG. 5 shows a transverse cross-section of typical fruit internal coloration and core size.
Figure 6:
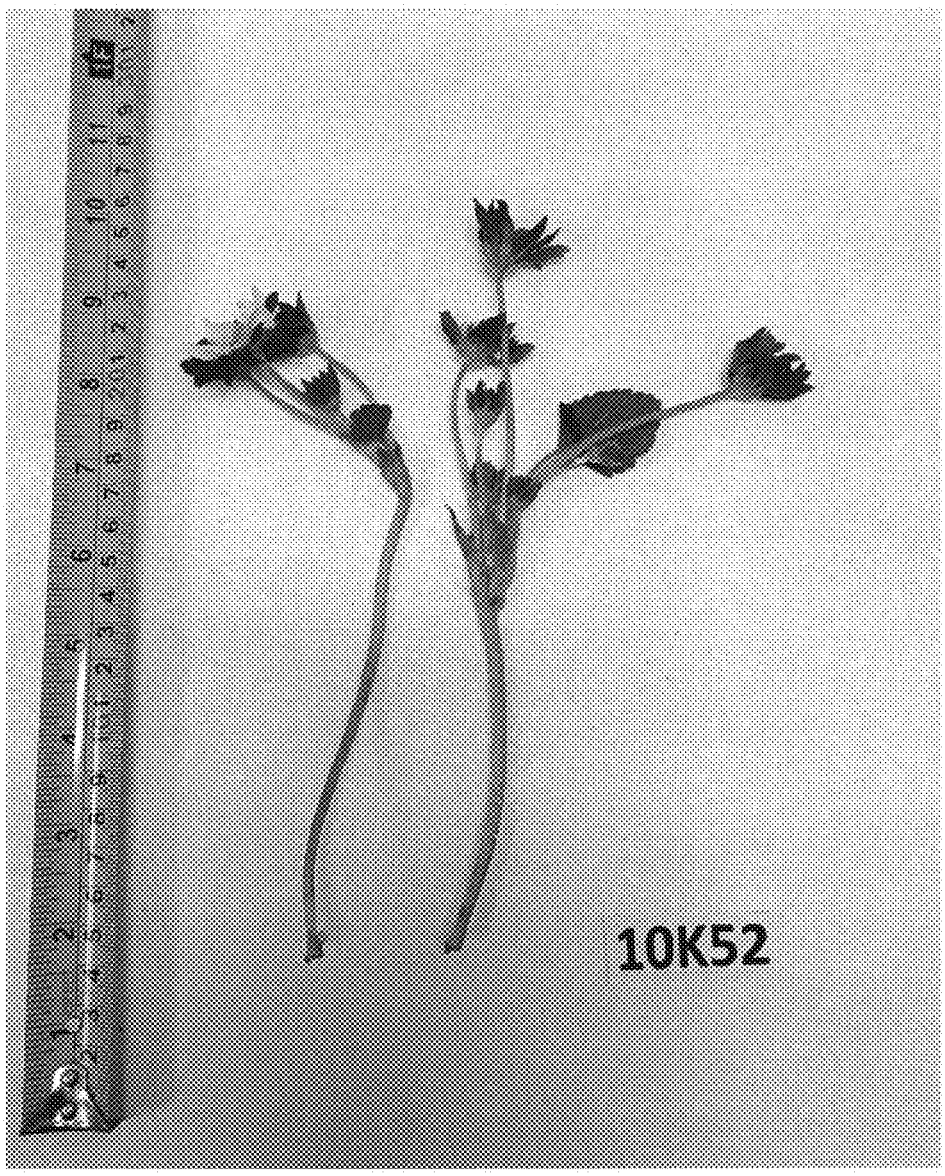
FIG. 6 shows typical inflorescences.
Figure 7:
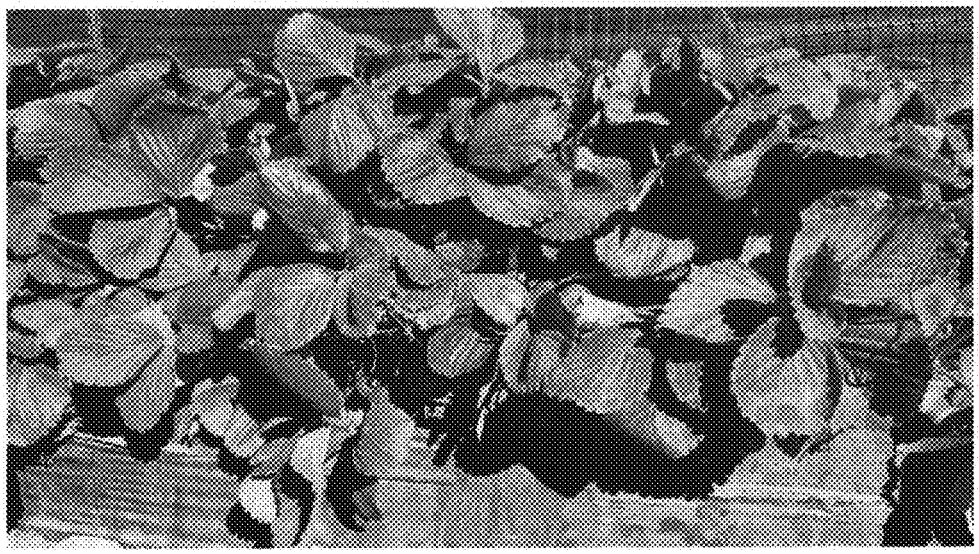
FIG. 7 shows typical late-season plants in a field.

'Sangria' is a new and distinct variety of strawberry (*Fragaria* x *ananassa*). It is the result of a cross between its female parent, '3F64,' and unreleased proprietary variety, and 'Sweet Ann,' it's male parent. '3F64' is a short-day variety, while 'Sweet Ann' is a day-neutral variety. 'Sangria' is a short-day variety that has partial remontant tendencies in temperate coastal environments. Plants have been observed blooming in production fields, but bloom only once in a high elevation nursery, consistent with a short-day variety. The plants of this new variety are of medium vigor, but produce multiple crowns early after planting. 'Sangria' exhibits several characteristics which are improvements over one or both of its parent varieties, and other known cultivars. The characteristics of 'Sangria' were observed in plants in late season.

The fruit size of 'Sangria' is large, larger than its '3F64' parent, but smaller than the fruit of 'Sweet Ann,' it's pollen parent. This smaller size of fruit relative to 'Sweet Ann' provides an advantage in packaging fruit where the sometimes overly large fruit of 'Sweet Ann' can be damaged when put into packaging to accommodate the fruit. The size, however, is still large enough where it can be seen, picked, and packaged quickly and efficiently.

'Sweet Ann' produces long conic fruit, while the fruit of 'Sangria' are long conic and sometimes wedge shaped. The fruit of 'Sangria' generally ripens more evenly from the tip to the shoulders of the berry, resulting in a more uniform red color over the whole fruit. In contrast, the shoulders of the fruit of 'Sweet Ann' are the last portion to ripen, and in certain conditions don't color at all. The fruit of 'Sangria' is mostly absent of creases and is generally smoother than the fruit of its parents, and is also firmer than its parents as well.

The data set forth for 'Sangria' in Table 1 was collected in October/November in 2017 from plants grown in a test plot in Moss Landing, Monterey County, Calif. Color terminology where noted is in accordance with the Pantone Color Formula Guide GP 1201.

TABLE 1

| Detailed Description of Characteristics of 'Sangria' | |
|---|---|
| SPECIFICATION: | |
| Genus/Species | *Fragaria x ananassa* |
| Market Name | Strawberry |

TABLE 1-continued

| Detailed Description of Characteristics of 'Sangria' | |
|---|---|
| PARENTS: | |
| Female | Proprietary variety '3F64' (Unpatented) |
| Male | 'Sweet Ann' (U.S. Plant Pat. No. 22,472). |
| PLANT: | |
| Type | Short Day. |
| Growth Habit | Semi-upright. |
| Foliage density | Medium. |
| Vigor | Medium. |
| Height | Average: 29.4 cm; range: 24 cm to 35 cm. |
| Width | Average: 47.1 cm; range: 43 cm to 51 cm. |
| Crowns | Multiple crowns produced early after planting. |
| Disease tolerance | Test plots showed moderate tolerance to *Macrophomina phaseolina* (Crown rot) and a moderate tolerance to *Verticillium dahliae*. |
| LEAF: | |
| Width | Average: 134 mm; range: 120 mm to 170 mm. |
| Color | Adaxial surface: green 350 C. Abaxial surface: green 370 U. |
| Pubescens | Light density. |
| Inter-vein blistering | Low-moderate. |
| Glossiness | Medium. |
| Variegation | None. |
| TERMINAL LEAFLET: | |
| Length | Average: 84.8 mm; range: 60 mm to 100 mm. |
| Width | Average: 74.3 mm; range: 58 mm to 91 mm. |
| Ratio length to width | 1.14. |
| Margins | Serrate to crenate. |
| Leaf shape | Orbicular. |
| Base shape | Rounded to obtuse. |
| Cross-section shape | Slightly concave, to slightly convex. |
| PETIOLE: | |
| Pubescens | Medium density; direction: perpendicular. |
| Petiole color | Green 382 U. |
| Petiole length | Average: 19.8 cm; Range: 16 cm to 25.5 cm. |
| Petiole diameter | Average: 3.38 mm; Range: 2.82 mm to 4.05 mm. |
| STIPULE: | |
| Anthocyanin coloration | Absent. |
| Length | Average: 36.6 mm; Range: 24 mm to 44 mm. |
| Width | Average: 9.4 mm; Range: 7 mm to 12 mm. |
| STOLEN: | |
| Anthocyanin coloration | Present. |
| Pubescens | Medium; upward to perpendicular direction. |
| Diameter | Average: 2.85 mm; Range: 2.11 mm to 3.35 mm. |
| INFLORESCENCE: | |
| Flowering time | Fairly early. |
| Position | Slightly below the canopy, but visible. |
| Number of blooms | Average: 5.2; Range: 3 to 7. |
| Length | Average: 24.4 cm; Range: 16 cm to 33.5 cm, |
| Flower | Average diameter: 29.2 mm; Range: 24 mm to 34 mm. |

TABLE 1-continued

| Detailed Description of Characteristics of 'Sangria' | |
|---|---|
| Petal arrangement | Mostly overlapping. |
| Petal number | Average: 5.7; Range: 5 to 7. |
| Petal length | Average: 15.3 mm; Range: 13 mm to 17 mm. |
| Petal width | Average: 13.6 mm; Range: 12 mm to 15 mm. |
| Ratio length to width | 1.125. |
| Petal color | Bright white 11-0601 TPX. |
| Calyx | Larger than the corolla. |
| Calyx color | Adaxial surface: green 364 C. Abaxial Surface: green 377 U. |
| Stamens | Average number: 33; Range: 30 to 37. |
| Pedicel | Attitude of hairs is upward. |
| FRUIT | |
| Bearing | Short-day, but partially remontant in cool coastal environments. |
| Shape | Long conical to occasionally wedge. |
| Length | Average: 48.5 mm; Range: 45 mm to 55 mm. |
| Width | Average: 39.2 mm; Range: 35 mm to 48 mm. |
| Ratio length to width | 1.24. |
| Size | Seasonal average: 24 g per berry. |
| Achenes | Sunken, approximately level with the fruit surface. |
| Glossiness | Semi-glossy. |
| External color | Red 200 C. |
| Internal color | Flesh (excluding core): Red 032 U. |
| Evenness of external color | Even, slight band of no color near calyx. |
| Width of band at top devoid of achenes | Small. |
| Fruit center | Some hollowness. |
| Yield | Average grams per plant: 1507 g. |
| Firmness | Medium-firm, firmer than parent and cultivar 'Sweet Ann' |
| % Brix | Average: 9.5; Range: 8.6-10.6. |

The comparison statistics set forth in the following tables are with respect to characteristics observed in late season of 'Sangria.' All measurements of 'Sangria' were taken in Moss Landing, Calif. in 2017. In Table 2 and 3, the characteristics of 'Sangria' are compared with the varieties 'Sweet Ann' and 'Lucia' (U.S. Plant Pat. No. 26,974) historical data. Color identifications where noted are in accordance with the Pantone Color Formula Guide.

Plants and Foliage

The form and structure of the plants of 'Sangria' are similar to that of 'Sweet Ann' plants: erect and open. However, the plants of 'Sangria' are much smaller than those of 'Sweet Ann.' The plants of 'Sangria,' unlike those of 'Sweet Ann,' are more moderately vigorous in growth habit. They are more closely related in vigor to many other commercial cultivars grown in fresh strawberry production fields in California. The leaves of 'Sangria' also have a higher proportion of having four leaflets, as opposed to the common number of three. While it is still a rare occurrence, it is still noticeable that they occur more frequently than in other common cultivars.

TABLE 2

Foliar Characteristics of 'Sangria' Compared to 'Sweet Ann' and 'Lucia'

| Foliar Characteristics | | Cultivar 'Sangria' | 'Lucia' | 'Sweet Ann' |
|---|---|---|---|---|
| Plant height (mm) | Average | 294 | 391 | 380 |
| | Range | 240-350 | 292-490 | 290-480 |
| Plant spread (mm) | Average | 471 | 4/2 | 420 |
| | Range | 430-510 | 430-550 | 330-510 |
| Leaf width (mm) | Average | 134 | 195 | 165 |
| | Range | 120-170 | 165-220 | 130-195 |
| Mid-tier leaflet length (mm) | Average | 85 | 103 | 88 |
| | Range | 60-100 | 82-116 | 72-105 |
| Mid-tier leaflet width (mm) | Average | 74 | 91 | 67 |
| | Range | 58-91 | 73-102 | 52-88 |
| Petiole length (mm) | Average | 198 | 268 | 220 |
| | Range | 160-255 | 230-335 | 150-280 |
| Petiole diameter (mm) | Average | 3.38 | 4.48 | 3.74 |
| | Range | 3.09-4.05 | 3.70-5.80 | 3.01-429 |
| Number of leaflets per leaf | | Mostly 3, few 4 | 3 | 3 |
| Leaflet convexity | | Concave to convex | Slight concave | Slight concave |
| Shape of leaflet base | | Round to obtuse | Rounded to obtuse | Obtuse |
| Leaflet pubescence | | Light | Medium | Medium |
| Petiole pubescence | | Medium | Medium | Medium |
| Direction | | Perpen-dicular | Perpen-dicular | Perpen-dicular |
| Stipule length (mm) | Average | 36.6 | 35.7 | Not available |
| | Range | 24-44 | 1040 | |
| Stipule anthocyanin coloration | | No | Yes | Yes-weak |
| Leaflet margins | | Serrate to crenate | Serrate to crenate | Commonly crenate |
| Leaflet color adaxial surface | | 350 C | 364U | 364 U |
| Leaflet color abaxial surface | | 370 U | 363U | 370 U |
| Petiole color | | 382 U | 366U | 383 U |
| Leaflet surface blistering | | Slight-medium | Medium | Very weak |
| Leaflet surface glossiness | | Medium | High | Medium |

Flowers and Fruit

'Sangria' is a short-day variety that has partial remontant tendencies under certain temperature and horticultural conditions; mainly cooler coastal environments. While 'Lucia' and 'Sweet Ann' have longer inflorescences as compared to 'Sangria,' when compared to the plant size, all three varieties produce flowers that are visible within or above the canopy level, leaving flowers exposed to pollinators. The petals of 'Sangria' are also bigger than those of 'Sweet Ann' or 'Lucia.' The light red exterior color of the fruit of 'Sangria' is slightly darker than that of 'Lucia,' but of similar color to that of 'Sweet Ann.' The culinary qualities of all three varieties are good, including: good shape and size, light red color, and a good strawberry flavor.

In Table 3, comparative data for flower and fruit characteristics for 'Sangria,' 'Lucia,' and 'Sweet Ann' are set forth.

TABLE 3

Flower and Fruit Characteristics of 'Sangria' Compared to 'Lucia' and 'Sweet Ann'

| Chararteristic | | Cultivar 'Sangria' | 'Lucia' | 'Sweet Ann' |
|---|---|---|---|---|
| Petal number | Average | 5.7 | 5 | 5.4 |
| | Range | 5-7 | 5 | 5-6 |
| Petal length (mm) | Average | 15.3 | 12.44 | 11.21 |
| | Range | 13-17 | 10.6-14.3 | 9.2-13 |
| Petal width (mm) | Average | 13.6 | 11.86 | 11.1 |
| | Range | 12-15 | 10-13 | 9-13 |
| Position of flower (relative to canopy) | | Most exposed, some below | mostly exposed | most exposed, some even |
| Pedicel length (mm) | Average | 244 | 430 | 330 |
| | Range | 160-335 | 380-540 | 240-420 |
| Sepal color | Adaxial | 364 C | 364 U | 364 U |
| | Abaxial | 377 U | 371 U | 370 U |
| Corolla diameter (mm) | Average | 29.2 | 28.2 | 30.3 |
| | Range | 24-34 | 23.5-34 | 27-33 |
| Fruit color | External | 200 C | 1788 C | 185 C |
| | Internal | 032 IJ | 179 C | 1788 C |

Leaf samples from 'Sangria,' along with three other patented selections from the breeding program including 'Lucia,' 'Scarlet,' (U.S. Plant Pat. No. 27,034) and 'Ruby June' (U.S. Plant Pat. No. 27,190) were submitted to a lab for allelic fingerprint comparison to over two hundred other varieties of strawberry in its database. The allelic fingerprint analysis establishes that 'Sangria' is distinct and unique compared to the lab's large database of allelic fingerprints. Table 4 sets forth test results of three markers which differentiate 'Sangria.'

TABLE 4

Allelic Fingerprint Analysis

| Cultivar | Marker 1 | Marker 2 | Marker 3 |
|---|---|---|---|
| 'Sangria' | 204, 206, 229 | 190, 216 | 279, 289 |
| 'Lucia' | 202, 204, 206, 229 | 188, 216, 232 | 279, 281, 289 |
| 'Scarlet' | 204, 206, 214, 229 | 173, 190, 232 | 279, 281, 289 |
| 'Ruby June' | 206, 224, 229 | 188, 190, 216, 232 | 279, 289 |

Performance

Performance with respect to fruit size, yield and appearance for 'Sangria' was assessed by making comparisons with several other varieties in the breeding program, including 'Sweet Ann,' 'Lucia,' 'Ruby June,' and 'Scarlet.' All the plants for this trial were initially grown at a high elevation nursery in Macdoel, Siskiyou County, Calif. Plants of 'Sangria' and the comparison varieties were then planted and evaluated in a test plot in Moss Landing, Monterey County, Calif. in the end of 2016 through 2017.

Of the varieties tested, 'Sangria' performed similarly to three of the four varieties tested, with an average seasonal yield of 1,507 grams per plant, beating out 'Scarlet' slightly (1,460 grams/plant) and closely behind 'Ruby June' (1,597 grams/plant) and 'Lucia' (1,584 grams/plant). Only the day-neutral 'Sweet Ann' out performed 'Sangria' in seasonal yield per plant with an average of 2,003 grams per plant. The average fruit weight of 'Sangria' fell between 'Ruby June' (23 grams) and 'Lucia' (25 grams).

The fruit of 'Sangria' was also rated based upon commercial appeal on a scale of 1 (worst) to 5 (best) along with several other varieties. 'Sangria' had a high score of 4.0, which tied it with 'Sweet Ann,' which was better than both 'Ruby June' (3.75) and 'Scarlet' (3.5). Only 'Lucia' outperformed 'Sangria' in this comparison with a rating of 4.5, due mainly to its near uniform berries with very few creases.

Table 5 shows the fruit performance of 'Sangria' as compared to 'Sweet Ann,' 'Lucia,' 'Ruby June,' and 'Scarlet.'

TABLE 5

Comparison of Performance of 'Sangria' to Other Varieties

| Cultivar | Seasonal Yield grams/plant | Seasonal Average berry weight grams/berry | Appearance Score Rating 5 = Best |
|---|---|---|---|
| 'Sangria' | 1,507 | 24 | 4.0 |
| 'Sweet Ann' | 2,003 | 31 | 4.0 |

TABLE 5-continued

Comparison of Performance of 'Sangria' to Other Varieties

| Cultivar | Seasonal Yield grams/plant | Seasonal Average berry weight grams/berry | Appearance Score Rating 5 = Best |
|---|---|---|---|
| 'Ruby June' | 1,597 | 23 | 3.75 |
| 'Lucia' | 1,584 | 25 | 4.5 |
| 'Scarlet' | 1,460 | 27 | 3.5 |

I claim:

1. A new and distinct strawberry plant named 'Sangria' as described and illustrated.

* * * * *